United States Patent [19]

Udaka et al.

[11] Patent Number: 5,714,346
[45] Date of Patent: Feb. 3, 1998

[54] **PROCESS FOR PRODUCTION OF HUMAN GROWTH HORMONE USING *BACILLUS BREVIS***

[75] Inventors: Shigezo Udaka, Nagoya; Tsutomu Kajino, Aichi-gun; Yoko Saito, Aichi-gun; Masana Hirai, Aichi-gun; Yukio Yamada, Aichi-gun; Fumihiko Hoshino, Aichi-gun, all of Japan

[73] Assignee: Sumitomo Pharmaceuticals Company, Limited, Osaka, Japan

[21] Appl. No.: 507,313

[22] PCT Filed: Feb. 22, 1994

[86] PCT No.: PCT/JP94/00269

§ 371 Date: Aug. 22, 1995

§ 102(e) Date: Aug. 22, 1995

[87] PCT Pub. No.: WO94/19474

PCT Pub. Date: Sep. 1, 1995

[30] Foreign Application Priority Data

| Feb. 22, 1993 | [JP] | Japan | 5-032083 |
| Feb. 22, 1993 | [JP] | Japan | 5-032090 |

[51] Int. Cl.$^6$ ............ C12P 21/06; C12N 1/20; C07H 21/04
[52] U.S. Cl. .............. 435/69.1; 435/252.31; 536/24.1
[58] Field of Search .......... 435/69.1, 252.31; 536/24.1

[56] References Cited

U.S. PATENT DOCUMENTS

| 4,977,089 | 12/1990 | Kovacevic et al. | 435/252.31 |
| 4,994,380 | 2/1991 | Udaka et al. | 435/69.1 |
| 5,032,510 | 7/1991 | Kovacevic et al. | 435/69.1 |
| 5,232,841 | 8/1993 | Hashimoto et al. | 435/69.8 |

FOREIGN PATENT DOCUMENTS

| 326 046 A2 | 8/1988 | European Pat. Off. |
| 4-304889 | 10/1992 | Japan |
| 9419474 | 1/1994 | WIPO |

OTHER PUBLICATIONS

Nakayama et al., "Efficient secretion of the authentic mature human growth hormone by *Bacillus subtilis*," *Journal of Biotechnology* 8(2): 123–134, 1988.

Hikita and Mizushima, "Effects of Total Hydrophobicity and Length of the Hydrophobic Domain of a Signal Peptide on in Vitro Translocation Efficiency," *Journal of Biological Chemistry* 267(7): 4882–4888, 1992.

Sasaki et al., "In Vitro Kinetic Analysis of the Role of the Positive Charge at the Amino-terminal Region of Signal Peptides in Translocation of Secretory Protein across the Cytoplasmic Membrane in *Escherichia coli*," *Journal of Biological Chemistry* 265(8): 4358–4363, 1990.

Seeburg, P., "The Human Growth Hormone Gene Family: Nucleotide Sequences Show Recent Divergence and Predict a New Polypeptide Hormone," *DNA* 1(3): 239–249, 1982.

Takemura et al., "Production and secretion of human interleukin-2 by *Bacillus brevis*," *Nippon Nogeikagaku Kaisha* 66(3): 296, abstract #3Zp19, 1992. (English Translation Included Herewith).

Yamagata et al., "Use of *Bacillus brevis* for efficient synthesis and secretion of human epidermal growth factor," *Proc. Natl. Acad. Sci. USA* 86: 3589–3593, 1989.

Adachi et al., 1990, J. Bacteriology, 172(1):511–513.

*Primary Examiner*—Douglas W. Robinson
*Assistant Examiner*—Thanda Wai
*Attorney, Agent, or Firm*—Seed and Berry LLP

[57] ABSTRACT

A host-vector system suitable for production of human growth hormone (hGH) and a process for production of hGH using the same are provided. As an hGH expression plasmid, a recombinant DNA wherein a DNA coding for hGH is linked to the 3'-terminal of a DNA containing a promoter region derived from *Bacillus brevis* is provided, and as a host, especially a mutant *Bacillus brevis* substantially not exhibiting protease activity to hGH is provided. A microorganism obtained by transforming said host with said hGH expression plasmid efficiently produces hGH when it is cultured.

9 Claims, 6 Drawing Sheets

WESTERN BLOTTING

LANE 1 ... hGH PRODUCED BY TRANSFORMED B. brevis 31-OK

LANE 2 ... STANDARD hGH

LANE 1 ... MOLECULAR WEIGHT MARKER
LANE 2 ... STANDARD PREPARATION (REDUCING)
LANE 3 ... PURIFIED PREPARATION (REDUCING)
LANE 4 ... STANDARD PREPARATION (NON-REDUCING)
LANE 5 ... PURIFIED PREPARATION (NON-REDUCING)

MWP

SEQ. ID NO. 1  5' ATGAAAAAGGTCGTTAACAGTGTATTGGCTAGTGCACTCGCACTTACTGTTGCTCCATGGCTTTCGCTGCAG 3'

SEQ. ID NO. 5     MetLysLysValValAsnSerValLeuAlaSerAlaLeuAlaLeuThrValAlaProMetAlaPheAlaAla (Labels above sequence: HpaI, ApaLI, NcoI, PstI)

R2L4

SEQ. ID NO. 2  5' ATGAAAAAAAAGAAGGGTCGTTAACAGTATTGCTTCTCGCTAGCACTAGTGTTGCTCCATGGCTTTCGCTGCAG 3'

SEQ. ID NO. 6     MetLysLys​ArgArg​ValValAsnSerValLeu​LeuLeuLeu​AlaSerAlaLeuAlaLeuThrValAlaProMetAlaPheAla (Labels above sequence: HpaI, ApaLI, NcoI, PstI)

SYNTHETIC OLIGONUCLEOTIDE

R2 : 5' CACTGTTAACGACCCTTCTTTTTTCATGACCTTGTGTTC 3' (40mer) (SEQ ID NO: 3)

L4 : 5' CCGTGCACTAGCTAGCAGAAGCAATACACTGTTAACG 3' (37mer) (SEQ ID NO: 4)

*Fig. 6*

PROCESS FOR PRODUCTION OF HUMAN GROWTH HORMONE USING *BACILLUS BREVIS*

This application is a 371 of PCT/JP94/00269, filed Feb. 22, 1994.

1. Field of Art

The present invention relates to a process for production of human growth hormone (hereinafter sometimes referred to as "hGH") by *Bacillus brevis* carrying a DNA coding for hGH as a heterologous gene, as well as said DNA and *Bacillus brevis* carrying said DNA.

2. Background Art

The hGH comprises 191 amino acids, and the amino acid sequence thereof is already known (Bancroft, F. C., *Expl. Cell Res.*, 79, 275–278 (1973), or David V. Goeddel et al., *Nature*, 281, 544–548 (1979)). Since this substance has growth-stimulating action, action in fat-metabolism or action in sugar-metabolism, for a long time it has been used as a therapeutic agent for dwarfism, and recently it has been noticed as a therapeutic agent for senile dementia.

So far, much recombinant DNA research has been carried out using *E. coli*, and many heterogeneous proteins have been produced in *E. coli*. However, in this method, since the heterologous protein produced is intracellularly accumulated, not only are extraction of a desired product from the cells and the purification of the desired product from the extract time- and labor-consuming, but also it is not easy to recover the desired product in its native form.

On the other hand, for a long time, microorganisms belonging to the genus Bacillus have been industrially used as producers for various extracellular enzymes. Among these extracellular enzymes, α-amylase gene of *Bacillus amyloliquefaciens* (I. Palva et al., *Gene*, 22, 229 (1983)), penicillinase gene of *Bacillus licheniformis* (C. Chang et al., *Molecular Cloning and Gene Regulation in Bacilli*, Academic Press, 659 (1982)), and α-amylase gene of *Bacillus subtilis* (H. Yamazaki et al., *J. Bacteriol.*, 156, 327 (1983) have been cloned, and production and secretion of heterogeneous proteins using promoters or signal peptides of the above genes have been reported.

For the production and secretion of heterogeneous proteins by the genus Bacillus, *Bacillus subtilis* is mainly used as a host. However, since this microorganism produces a large amount of extracellular proteases, there is a tendency for heterogeneous proteins secreted by a recombinant DNA technique to be degraded and the amount accumulated is notably decreased.

On the contrary, Udaka et al. succeeded to produce and secrete α-amylase (Japanese Unexamined Patent Publication (Kokai) No. 62-201,583;, H. Yamagata et al., *J. Bacteriol.*, 169, 1239 (1987)), and swine pepsinogen (Shigezo Udaka, the abstracts of the 1987 Meeting of the Agricultural Chemical Society of Japan, p 837 to p 838; Norihiro Tsukagoshi, Nippon Nogei Kagaku Kaishi, 61, 68 (1987), using a promoter and signal peptide of MWP (Middle Wall Protein) (H. Yamagata et al., *J. Bacteriol.*, 169, 1239 (1987); Norihiro Tsukagoshi, Nippon Nogei Kagaku Kaishi, 61, 68 (1987)), which is a major extracellular protein of the above-mentioned microorganism, using as a host *Bacillus brevis* 47 which substantially does not extracellularly produce proteases (Japanese Unexamined Patent Publication (Kokai) Nos. 60-58,074, and 62-201,583; FERMP-7224).

In addition, Udaka et al. succeeded in isolating *Bacillus brevis* HPD31 (FERMBP-1087) producing no detectable extracellular protease, and in using it as a host so as to produce thermostable α-amylase (Japanese Unexamined Patent Publication (Kokai) No. 63-56,277; the abstracts of the 1987 Agricultural Chemical Society of Japan), and human EGF (H. Yamagata et al., *Proc. Natl. Acad. Sci. USA*, 86, 3589 (1989); Japanese Unexamined Patent Publication (Kokai) No. 2-31,682).

The production of hGH using as a host *E. coli* (David V. Geoddel et al., *Nature*, 281, 544–548 (1979), Chang C. N. et al., *Gene*, 55, 189–196 (1987)), *Bacillus subtilis* (M. Honjo et al., *J. Biotech.*, 6, 191–204 (1987)), yeast (R. Hiramatsu et al., *Appl. Environ. Microbiol.*, 57, 2052–2056 (1991)) or animal cells (Lupker J. H. et al., *Gene*, 24, 281–287 (1983)) has been reported.

DISCLOSURE OF THE INVENTION

As described above, although it has been attempted to produce hGH using as a host *E. coli*, yeast or animal cells, all of these procedures are not satisfactory due to the complicated purification process, low productivity, etc. Accordingly, the purpose of the invention is to provide a process for efficiently producing hGH using a host-vector system which allows an efficient production of hGH.

Udaka et al. seeked to develop host-vector systems for the production of heterogeneous proteins, found that *Bacillus brevis* can be advantageously used as a host, and proposed the use thereof for production of several heterogeneous proteins (for example, Japanese Unexamined Patent Publication (Kokai) No. 63-56,277). On the other hand, the present inventors extensively investigated the creation of recombinant plasmids capable of efficiently expressing DNA coding for hGH using the above-mentioned hosts, and found that the use of a promoter derived from *Bacillus brevis* which is to be used as a host, and of DNA necessary for secretion in a particular manner is effective for the expression of hGH.

Accordingly, the above-mentioned purpose is achieved by the use of a recombinant DNA wherein a DNA coding for hGH is linked to the 3'-terminal of a DNA containing a promoter region derived from *Bacillus brevis*. Namely, according to the present invention, provided are the above-mentioned recombinant DNA, *Bacillus brevis* carrying the recombinant DNA, and a process for production of hGH characterized by culturing said *Bacillus brevis* in a nutrient medium and recovering the hGH from the culture.

DNA coding for hGH used in the present invention is either DNA directly isolated from the human pituitary gland, or DNA chemical synthesized on the basis of known amino acid sequence of hGH (Ikehara et al., *Proc. Natl. Acad. Sci. USA*, 81, 5956 (1984)). Any promoter functional in *Bacillus brevis* (hereinafter, sometimes abbreviated as *B. brevis*) and derived from any strain belonging to *B. brevis* can be used. For example, as a specific embodiment, a promoter of major extracellular protein gene of *B. brevis* 47 (FERM-7224) or *B. brevis* HPD31) (FERM BP-1087) can be used. It is essential that the DNA containing a promoter region further contains an SD sequence, a translation initiation codon, etc., in addition to the promoter, and further may contain a part of the major extracellular protein gene.

To join a DNA coding for hGH to the 3'-terminal of the DNA containing said promoter regions, a DNA coding for hGH may be joined to the 3'-terminal of DNA excised from the chromosome of *B. brevis* (T. Adachi et al., *J. Bacteriol.*, 171, 1010–1016 (1989)).

Although hGH can be intracellularly or extracellularly accumulated, if extracellular accumulation is intended, a region coding for a signal peptide must be included in a 3'-terminal side of a DNA containing a promoter region. As a signal peptide, for example, a signal peptide of a major extracellular protein of *B. brevis* 47 or *B. brevis* HPD31 may be mentioned. A specific example of signal peptide is that of MWP (Middle Wall Protein) of *B. brevis* 47.

An expression vector which contains the promoter region and is used for expression of an hGH gene is exemplified by pHY500 or pNU200 (Japanese Unexamined Patent Publication (Kokai) No. 2-31,682, Shigezo Udaka, Nippon Nogei Kagaku Kaishi, 61, 669 (1987)).

A method for construction of an expression plasmid for hGH is well known in the art and described, for example in Molecular Cloning 2nd. Ed., A Laboratory Manual (Cold Spring Harbor Laboratory (1990)), and therefore a desired recombinant DNA (expression plasmid for hGH) can be constructed according to the abovementioned procedure. As a preferable expression plasmid for hGH, pNU200-GH, etc., as prepared in the examples described hereinafter can be mentioned. A host useful for construction of the plasmids may be any microorganism belonging to *E. coli.*, *Bacillus subtilis* or *Bacillus brevis*, and for example, *E. coli* HB101, *E. coli* JM109, *Bacillus subtilis* RM141 (*J. Bacteriol.*, 158, 1054 (1984)), *B. brevis* 47 (FERMP-7224), etc., may be mentioned.

A host for expression of said gene may be any host which does not provide a strong negative influence on hGH produced by the expression of said expression plasmids, and may be *B. brevis* 47 (FERM P-7224), *B. brevis* 47-5 (FERM BP-1664), *B. brevis* HPD31 (FERM BP-1087) or the like. Especially preferable is *B. brevis* 31-OK (FERM BP-4573) obtained from the *B. brevis* HPD31 by mutagenesis. Since this mutant substantially does not exhibit protease activity on hGH, it can stably maintain hGH produced and accumulated in a culture (especially extracellularly).

The above-mentioned expression plasmid for hGH may be used to transform a host *B. brevis* according to the Takahashi's method (*J. Bacteriol.*, 156, 1130 (1983)) or by electroporation (H. Takagi et al., *Agric. Biol. Chem.*, 53, 3099–3100 (1989)).

A transformant thus constructed is cultured in a nutrient medium so as to produce a large amount of hGH, a major portion of which is extracellularly secreted. When the *B. brevis* 31-OK is used as a host, since hGH extracellularly secreted is stably maintained, the hGH can be efficiently recovered from the culture.

A nutrient medium used for culturing contains a carbon source, nitrogen source, and if necessary inorganic salts. In addition, culturing can be carried out using a synthetic medium comprising mainly a sugar and inorganic salts. When an auxotropic strain is used, a corresponding nutrient factor necessary for the growth is preferably added to the medium. In addition, if necessary, an antibiotic or antifoam is added to the medium. Regarding culturing conditions, an initial pH of the medium is adjusted to 5.0 to 9.0, preferably 6.5 to 7.5. Culturing temperature is usually 15° C., to 42° C., and preferably 24° to 37° C., and culturing time is usually 16 to 360 hours, and preferably 24 to 144 hours.

After finishing the culturing, to recover hGH from the culture, a supernatant and microbial cells are separated by, for example, centrifugation or filtration. Intracellularly produced hGH is extracted by disrupting the microbial cells according to a conventional method in the art, such as an ultrasonic treatment, French press method, etc., or optionally with further addition of surfactant. Next, hGH contained in a culture supernatant or a cell-free extract thus obtained is purified according to a conventional procedure for purification of protein, for example, salting out, isoelectric point precipitation, various chromatographies such as gel filtration chromatography, ion exchange chromatography or reversed phase chromatography or the like to obtain desired hGH.

The resulting hGH can be quantitated by an enzyme immunoassay using an anti-hGH antibody, or HPLC. In addition, hGH can be quantitated from 3T3-L1 cells differentiation activity to fat cells (Techniques for tissue culturing (see. Ed. 2, Nippon Soshiki Baiyo Gakukai)).

EXAMPLES

Next, the present invention is further definitely explained in these Examples.

Example 1. Construction of human growth hormone (hGH) expression vector and preparation of transformants A 565 bp HinfI-SalI fragment coding for hGH was isolated from plasmid pGH-L9 (see, Ikehara et al., *Proc. Natl. Acad. Sci. USA..*, 81, 5956–5960 (1984)). To join a signal peptide of MWP and hGH, a DNA linker was chemically synthesized. The synthetic linker and the HinfI-SalI fragment containing an hGH gene were joined by T4 DNA ligase to obtain a 596 bp NcoI-SalI fragment.

On the other hand, a 27 bp NcoI-SalI fragment was deleted from a plasmid pBR-AN2 (which maintains Pst I site of ampicillin resistance gene in pBR-AN3 described in Shin Seikagaku Jikken Koza 17 Biseibutsu Jikken Ho (1 Ed.) Nippon Seikagaku Kai, p.373–377 (1992)) containing a C-terminal region of a signal peptide of MWP (Middle Wall Protein) which is one of the major wall proteins of *Bacillus brevis* 47 (FERM p-7224), and the above-mentioned 596 bp NcoI-SalI fragment was inserted thereinto to obtain a plasmid pBR-AN2-GH.

The plasmid pBR-AN3-GH was treated with restriction enzymes ApaLI and HindIII to isolate a 656 bp ApaLI-HindIII fragment. On the other hand, plasmid pNU200 (see, Shigezo Udaka, Nippon Nogei Kagaku Kaishi, 61, 669–676 (1987)) was cleaved with restriction enzymes ApaLI and HindIII to obtain a larger fragment, which was then joined to the above-mentioned 656 bp AlaLI-HindIII fragment with T4 DNA ligase. The reaction mixture was used to transform *Bacillus brevis* 47-5 (FERM BP-1664, IFO 14698) according to the Takahashi's method (*J. Bacteriol.*, 156, 1130 (1983)). From the resulting erythromycin-resistant transformant, a plasmid was isolated according to an alkaline extraction method (see, Molecular Cloning 2nd ed., A Laboratory Manual, Cold Spring Harbor Laboratory (1989) ), and designated pNU200-GH.

Next, the plasmid pNU200-GH was cleaved with restriction enzymes ApaLI and BclI to obtain an ApaLI-BclI fragment containing the hGH gene. On the other hand, plasmid pNUR2L4 containing an improved signal sequence R2L4 (FIG. 5 (R2L4)) (SEQ ID No: 2), wherein three Leu residues had been added to the hydrophobic region of MWP signal sequence (FIG. 5 (MWP)) (SEQ ID No: 1) and two Arg residues had been added to the positive charge region of said MWP signal sequence, was cleaved with restriction enzymes ApaLI and BclI to obtain an ApaLI-BclI fragment of about 3.8 kbp. This DNA fragment was joined to the above-mentioned DNA fragment containing an hGH with T4 DNA ligase to obtain plasmid pNUR2L4-GH as described above.

According to the Takahashi's method (*J. Bacteriol.*, 156, 1130 (1983)), the above-mentioned plasmids pNU200-GH and pNUR2L4-GH were separately introduced into *Bacillus brevis* 31-OK (FERM BP-4573) to obtain transformants, from which stable strains were then isolated and designated *Bacillus brevis* 31-OK (pNU200-GH) and *Bacillus brevis* 31-OK (pNUR2L4-GH) respectively.

Example 2. Culturing of transformants and production and secretion of hGH

Transformants *Bacillus brevis* 31-OK (pNU200-GH) and *Bacillus brevis* 31-OK (pNUR2L4-GH) obtained in Example 1, as well as control strains *Bacillus brevis* 31-OK (pNU200) and *Bacillus brevis* 31-OK (pNUR2L4) were cultured in a medium comprising polypepton 3%, yeast extract 0.2%, glucose 3%, $MgSO_4.7H_2O$ 0.01%, $CaCl_2.7H_2O$ 0.01%, $MnSO_4.4H_2O$ 0.001%, $FeSO_4.7H_2O$ 0.001%, $ZnSO_4.7H_2O$ 0.0001% and erhythromycin 10 mg/L (pH 7.2) at 30° C. for 3 to 6 days.

The culture broth thus obtained were centrifuged to obtain supernatants which were then assayed for hGH concentration by an enzyme immunoassay using an anti-hGH antibody (Table 1). Note that, the standard hGH preparation used was purchased from Bioproducts Co. (Seikagaku Kogyo K.K.).

TABLE 1

Production and Secretion of hGH by Transformants

| Transformant | Days for Culturing | hGH (mg/L) |
|---|---|---|
| *Bacillus brevis* 31-OK(pNU200) | 6 | 0 |
| *Bacillus brevis* 31-OK(pNUR2L4) | 6 | 0 |
| *Bacillus brevis* 31-OK(pNU200-GH) | 3 | 6.7 |
| *Bacillus brevis* 31-OK(pNU200-GH) | 6 | 16.5 |
| *Bacillus brevis* 31-OK(pNUR2L4-GH) | 6 | 200 |

Figure 1:
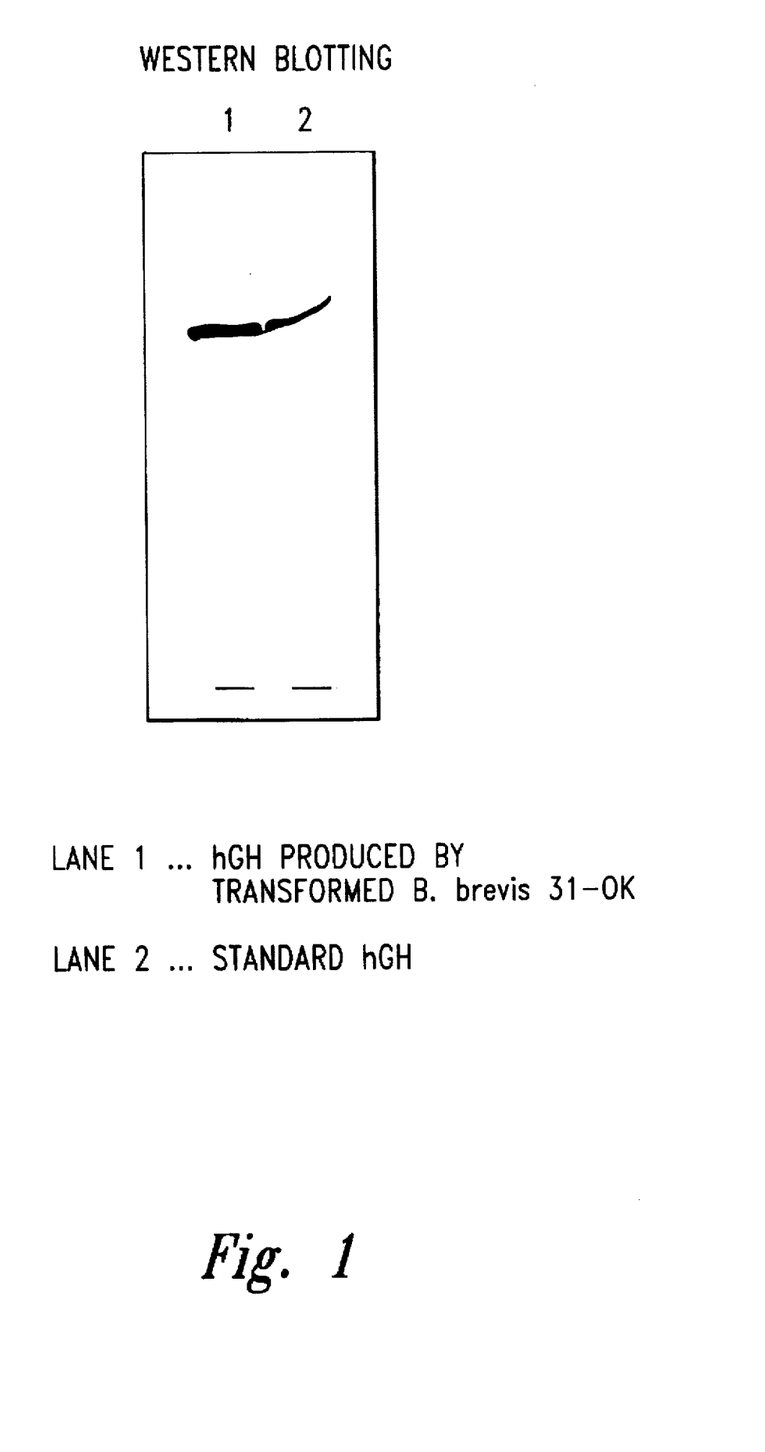
FIG. 1 represents the result of Western blotting after submitting a culture supernatant obtained in Example 2 and a standard hGH on SDS-polyacrylamide gel electrophoresis.

Next, the above-mentioned culture supernatants were subjected to an SDS-polyacrylamide gel electrophoresis according to the Laemmli's method (see, *Nature*, 227, 680 (1970)), and Western blotting was carried out according to the Burnette's method (*Anal. Biochem.*, 112, 195 (1981)) using an anti-hGH antibody. As a result, hGH was detected in the culture supernatants of *Bacillus brevis* 31-OK (pNU200-GH) and *Bacillus brevis* 31-OK (pNUR2L4-GH), and the molecular weight thereof conformed to that of the standard preparation (FIG. 1).

Example 3- Purification of hGH 100 ml of the culture supernatant obtained in Example 2 was pretreated by ultrafiltration (Fitron, Minisette Omega, 10k cut off), and purified by ion exchange chromatography (Pharmacia), reversed phase chromatography (Pharmacia) and reversed phase chromatography (Waters) so as to obtain 2.3 mg of a purified preparation of hGH.

Example 4. properties of purified hGH preparation

The properties of the purified hGH preparation obtained in Example 3 were as follows:

(1) Retention time in HPLC

Figure 2:
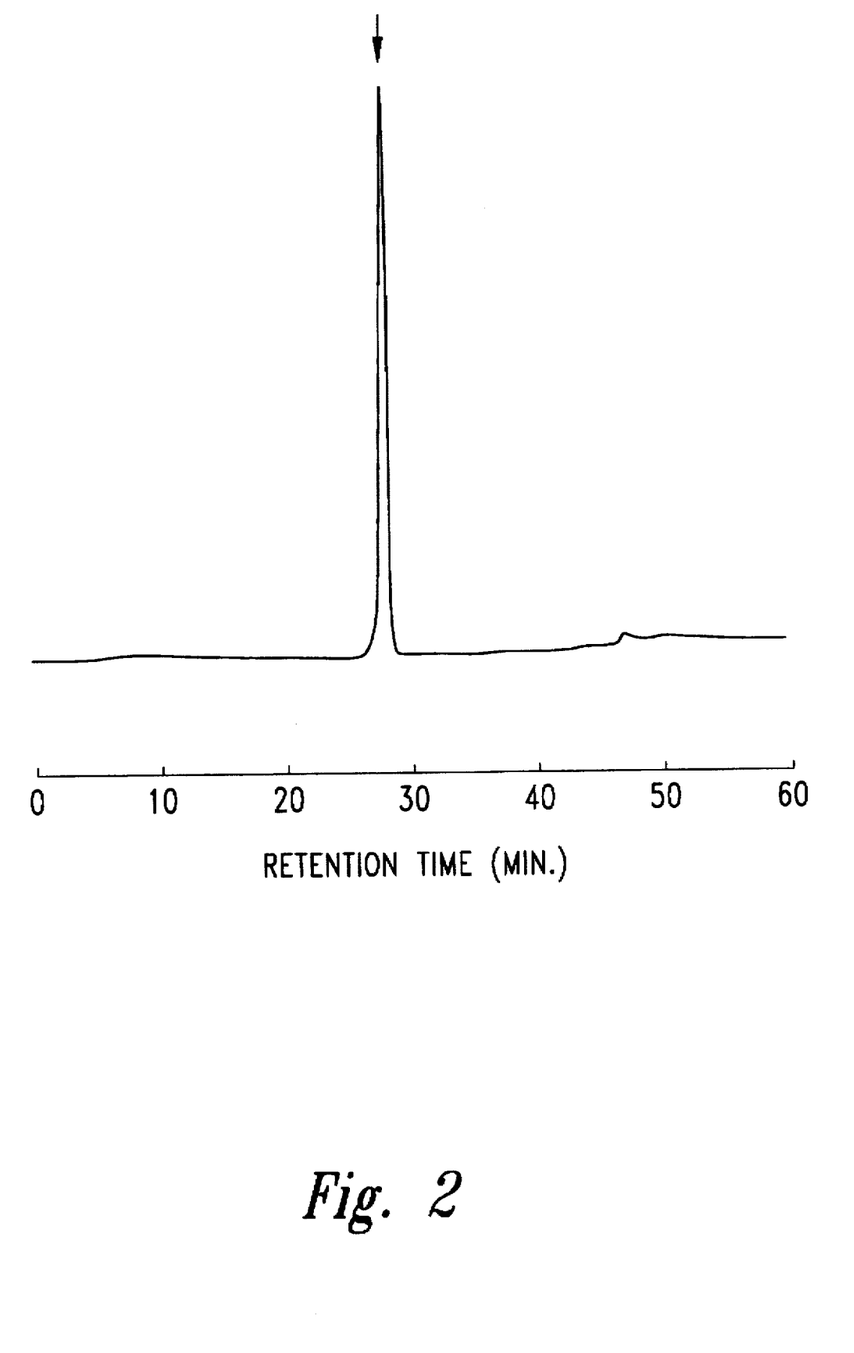
FIG. 2 represents the result of a reversed phase HPLC for a purified hGH product obtained in Example 4 (the abscissa axis shows retention time (min.), and the symbol arrow, shows the elution time (min.) of a standard hGH).

As a result of reverse phase HPLC, the purified hGH preparation obtained was substantially homogeneous (FIG. 2), and the retention time thereof conformed to that of the standard hGH preparation (a product of Bioproducts Co.).

Figure 3:
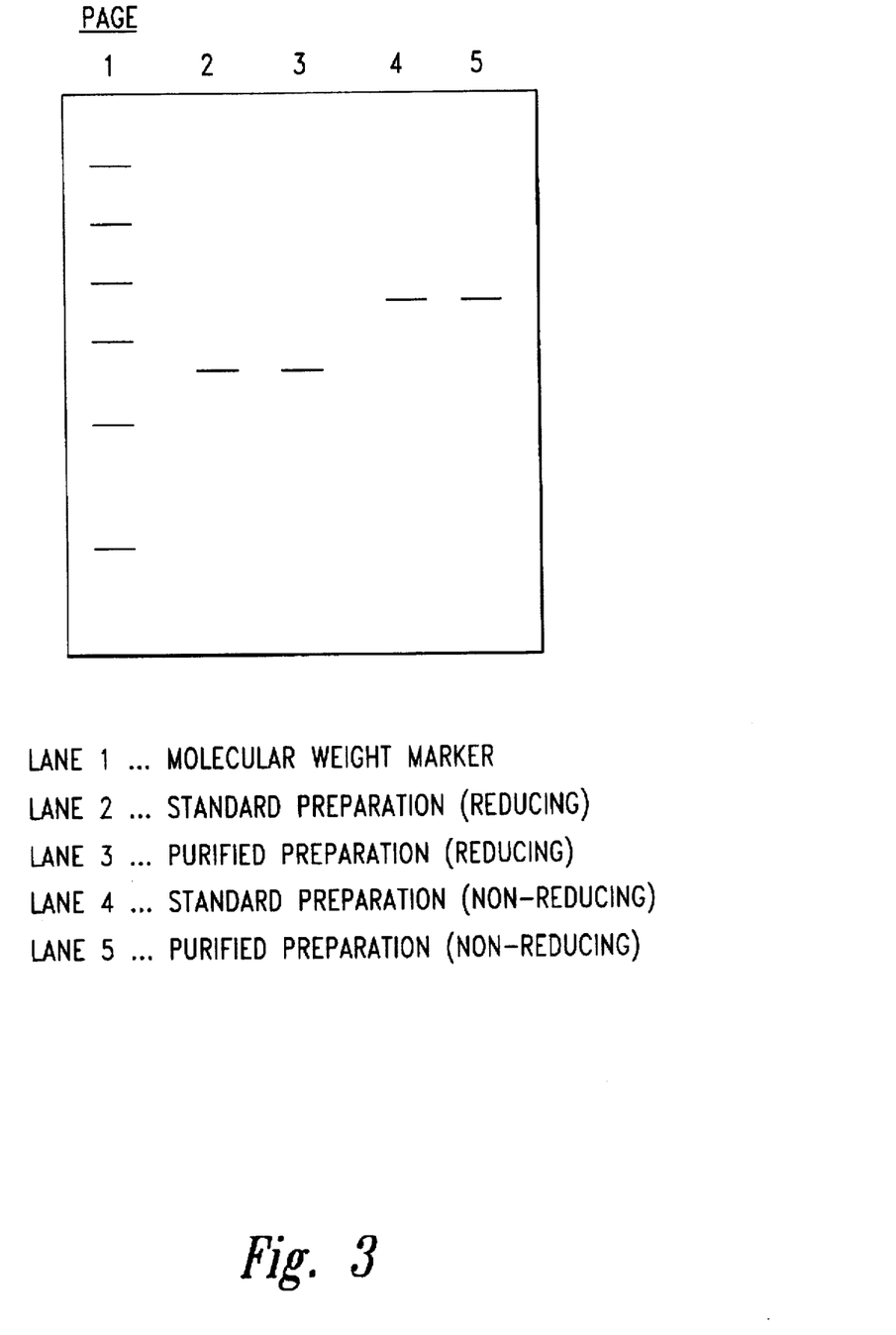
FIG. 3 represents the result of comparison between SDS-polyacrylamide gel electrophoresis patterns in reductive and non-reductive conditions for a purified hGH product obtained in Example 4 and a standard hGH.

(2) As a result by electrophoresis in 16% polyacrylamide gel containing 0.1% SDS, the purified preparation behaved in the same manner as the standard preparation both under a reducing condition and a nonreducing condition (FIG. 3).

(3) N-terminal amino acid sequence

As a result of analysis of N-terminal amino acid sequence of the purified preparation by pulse liquid automatic Edman degradation (Type 473A Applied Biosystems), the sequence of the purified preparation conformed to that of literature (see, Bancroft, F. C., *Expl. Cell Res.*, 79, 275-278(1973); David V. Goeddel et al., *Nature*, 281, 544-548 (1979)), as follows:

TABLE 2

| | N-terminal amino acid sequence | | | | | | | | | |
|---|---|---|---|---|---|---|---|---|---|---|
| | 1 | 2 | 3 | 4 | 5 | 6 | 7 | 8 | 9 | 10 |
| Purified preparation | Phe | Pro | Thr | Ile | Pro | Leu | Ser | Arg | Leu | Phe |
| Literature | Phe | Pro | Thr | Ile | Pro | Leu | Ser | Arg | Leu | Phe |

(4) Biological activity

Figure 4:
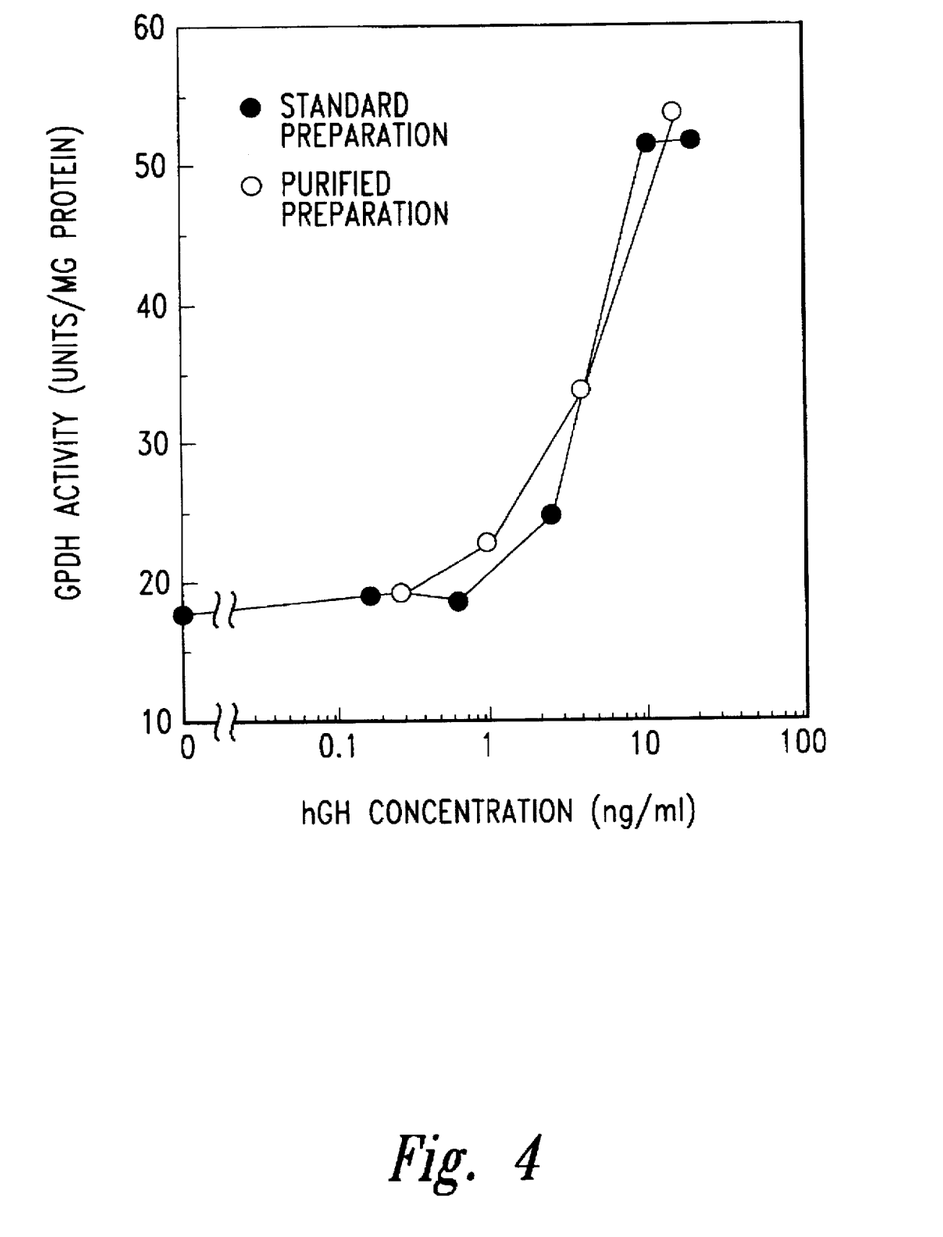
FIG. 4 is a graph comparing a purified hGH preparation obtained in Example 4 and a standard preparation for their biological activities for differentiation of 3T3-L1 cells to fat cells.

Biological activity of hGH was tested taking as an indication an activity to differentiate 3T3-L1 cells to fat cells (see, Techniques for tissue culturing (2) edited by Nippon Soshiki Baiyo Gakukai, p 110–115). As a result, the purified preparation exhibited the same biological activity as the standard preparation (FIG. 4).

Reference Example 1. Generation of *Bacillus brevis* 31-OK

The plasmid pNU200-GH obtained in Example 1 was introduced into a parent strain *Bacillus brevis* HPD31 (Japanese Unexamined Patent Publication (Kokai) No. 63–56,277, FERMBP-1087) to obtain *Bacillus brevis* HPD31 (pNU200GH). Cells of this transformant were diluted and suspended in T2 medium, and plated on a T2 plate, which was then irradiated with ultraviolet light (2J/m$^2$). The plate was incubated at 30° C. overnight, and resulting colonies were inoculated on a 5YC medium and cultured at 30° C. for 6 days. On the third day and sixth day samples of the culture were taken and an amount of hGH contained in culture supernatant was measured by enzyme immunoassay. In this case, one strain which provided an increase of the amount of hGH in culture supernatant between the third day and the sixth day was selected and isolated. When this mutant was compared with the parent strain, there was a remarkable difference in that the parent strain provided the decrease of the amount of hGH in culture supernatant between the third day and the sixth day, while the mutant exhibited an increase of the amount of hGH after the third day. To eliminate plasmid from the mutant, the mutant was repeatedly passaged in the erhythromycin-free T2 medium, and a strain which was sensitive to erhythromycin and did not produce hGH could be easily obtained. This strain was designated *Bacillus brevis* 31-OK.

The microbiological properties of the *Bacillus brevis* 31-OK (FERMBP-4573) were substantially the same as those of the parent strain *Bacillus brevis* HPD31 (see, Japanese Unexamined Patent Publication (Kokai) No. 63-56,277), except that these strains were different in an action to a particular heterogeneous protein. The main properties were as follows:

Physiological properties

| Physiological properties | |
| --- | --- |
| Reduction of nitrate | − |
| VP test for acetoin formation | − |
| Formation of indole | − |
| Formation of hydrogen sulfide | |
| TSI agar medium | − |
| Zinc acetate agar medium | + |
| Utilization of citrate | + |
| Utilization of inorganic nitrogen source | |
| Nitrate | − |
| Ammonium salt | + |
| Formation of pigments (King Medium) | − |
| Urease | − |
| Oxidase | + |
| Acylamidase | − |
| Catalase | + |
| O-F test | no-decomposition |
| Decomposition of gelatin | − |
| Formation of acid from glucose | − |
| Decomposition of xylose | − |
| Decomposition of lactose | − |
| Decomposition of maltose | − |
| Hydrolysis of arginine | − |
| pH allowing growth | 5.5 to 8.5 |

Morphological properties

| Size of cell | |
| --- | --- |
| in liquid medium: | 0.9 to 1.2 × 3.9 to 5.8 μm |
| on agar medium: | 0.9 to 1.2 × 2.9 to 4.2 μm |
| Shape of cell | rod |
| Polymorphism of cells | no |
| Motility | present |

Reference Example 2. preparation of plasmid pNUR2L4

Figure 5:
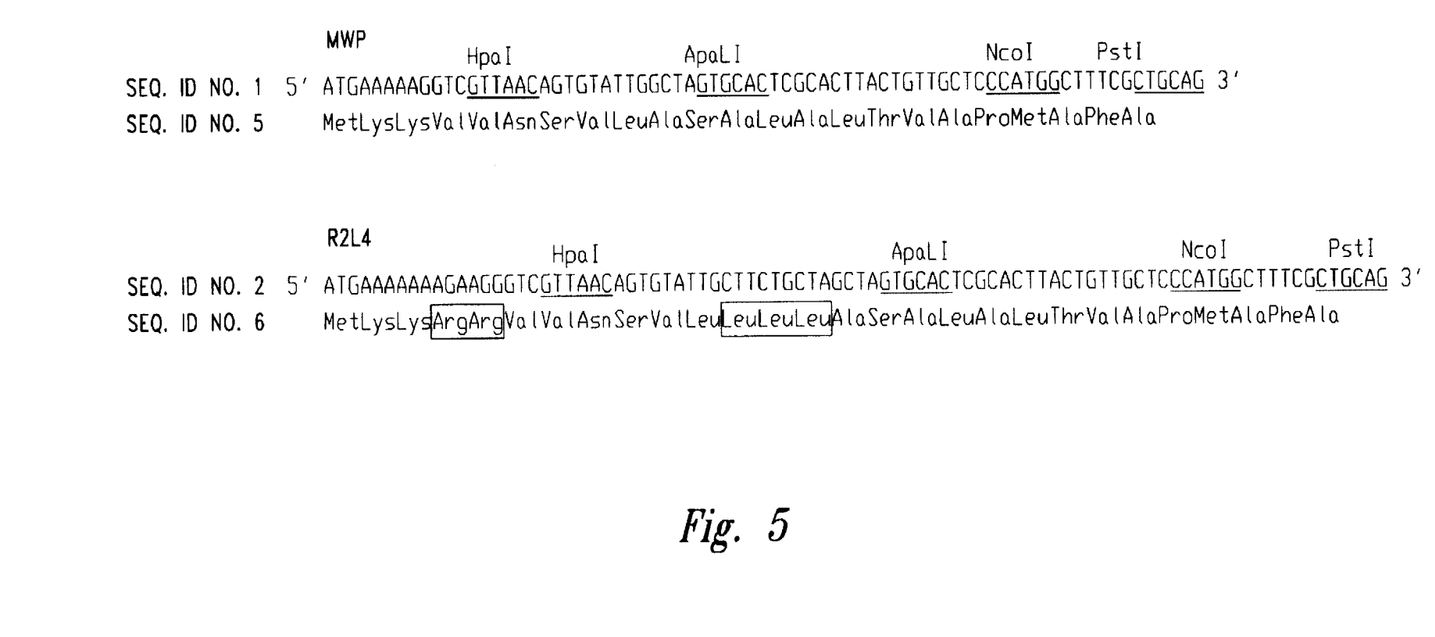
FIG. 5 represents a signal sequence of MWP of *Bacillus brevis* 47 (shown as MWP), and a signal sequence prepared by improvement of the MWP (the improved signal sequence is shown as R2L4).

(1) Construction of plasmid M13MWP pNU200 was digested with restriction enzymes EcoRI and HindIII (Takara Shuzo), and the resulting DNA fragment of about 670 bp was inserted into plasmid M13mp18 which had been digested with EcoRI and HindIII so as to obtain plasmid M13MWP. A nucleotide sequence from the MWP promoter to the signal sequence is shown in FIG. 5 (MWP) (SEQ ID NO: 1). The amino acid sequence encoded by such nucleotide sequence is also shown in FIG. 5 (SEQ ID NO: 5).

(2) Construction of plasmid M13R2

Figure 6:
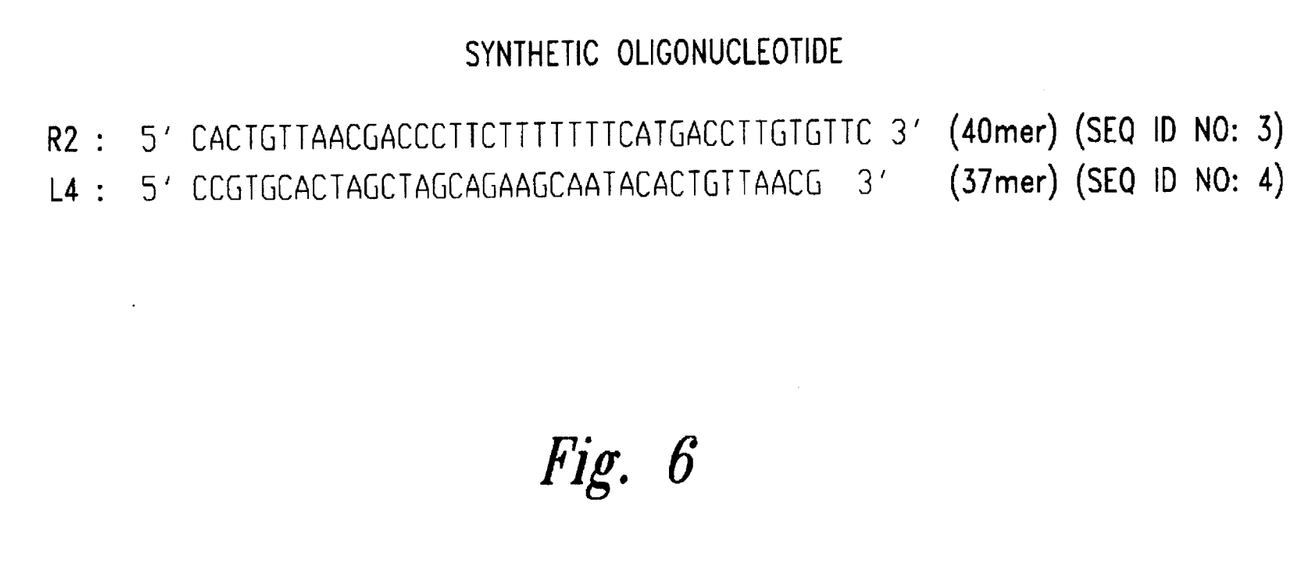
FIG. 6 represents nucleotide sequences of oligonucleotide primers used for site-specific mutagenesis of DNA coding for the signal sequence of MWP.

Site-specific mutagenesis was carried out using a single-stranded DNA of the M13MWP obtained above as a template, and using a synthetic primer R2 (FIG. 6) (SEQ ID NO: 3). The site-specific mutagenesis was carried out with an Amersham kit (Oligonucleotide-directed in vitro mutagenesis system, Amersham). Next, the nucleotide sequence of the DNA was confirmed, and a desired plasmid thus obtained was designated M13R2.

(3) Construction of plasmid M13L4

According to the procedure as described in Reference Example 2.(2), a single-stranded DNA of the plasmid M134 MWP as a template and a synthetic primer L4 (FIG. 6) (SEQ ID NO: 4) were used to obtain plasmid M13L4.

(4) Construction of plasmid pNUR2L4

The M13R2 obtained in (2) was digested with EcoRI and HpaI, and a 228 bp DNA fragment thus obtained and a 108 bp DNA fragment obtained by digesting the M13L4 obtained in (3) with HpaI and HindIII were inserted into pNU200 which had been digested with EcoRI and HindIII so as to obtain plasmid pNUR2L4. The nucleotide encoding signal sequence (R2L4) is shown in FIG. 5 (R2L4) (SEQ ID NO: 2). The amino acid sequence of the signal sequence (R2L4) is also shown in FIG. 5 (SEQ ID NO: 6).

INDUSTRIAL APPLICABILITY

According to the present invention, a host-vector system useful for efficient production of human growth hormone (hGH) is provided. Namely, hGH can be efficiently produced by using *Bacillus brevis* as a host and a recombinant DNA wherein a DNA coding for hGH is linked to the 3'-terminal of a DNA containing a promoter region derived from *Bacillus brevis* as an hGH expression plasmid. Especially, a mutant *Bacillus brevis* substantially not exhibiting protease activity to hGH is preferably used as a host.

Reference to deposited microorganisms according to the provision of Rule 13-2 of PCT.

Name of depository authority: National Institute of Bioscience and Human-Technology Agency of Industrial Science and Technology Address of depository authority: 1-3, Higashi 1-chome Tsukuba-shi Ibaraki-ken 305 Japan Deposition number and deposition date 1. FERM BP-1087 Jun. 24, 1986
2. FERM P-7224 Sep. 7, 1983
3. FERM BP-1664 Jan. 20, 1988
4. FERM BP-4573 Nov. 11, 1992

We claim:

1. A recombinant DNA wherein a DNA coding for human growth hormone is linked to the 3'-terminal of a DNA containing a promoter region derived from *Bacillus brevis* and wherein an improved signal sequence R2L4 (SEQ ID NO: 2) is contained in a 3'-terminal site of the DNA containing the promoter region.

2. A *Bacillus brevis* carrying a recombinant DNA wherein a DNA coding for human growth hormone is linked to the 3'-terminal of a DNA containing a promoter region derived from *Bacillus brevis* and wherein an improved signal sequence R2L4 (SEQ ID NO: 2) is contained in a 3'-terminal site of the DNA containing the promoter region.

3. A process for the production of human growth hormone characterized by culturing *Bacillus brevis* according to claim 2, and recovering human growth hormone from the culture.

4. A process for the production of human growth hormone characterized by culturing *Bacillus brevis* 31-OK (FERM BP-4573) carrying a recombinant DNA wherein a DNA coding for human growth hormone is linked to the 3'-terminal of a DNA containing a promoter region derived from *Bacillus brevis* and wherein a signal sequence of MWP (Middle Wall Protein) of *Bacillus brevis* is contained in a 3'-terminal site of the DNA containing the promoter region, and recovering human growth hormone from the culture.

5. A process for production of human growth hormone characterized by culturing *Bacillus brevis* 31-OK (FERM BP-4573) carrying a recombinant DNA wherein a DNA coding for human growth hormone is linked to the 3'-terminal of a DNA containing a promoter region derived from *Bacillus brevis* and wherein an improved signal sequence R2L4 (SEQ ID NO: 2) is contained in a 3'-terminal site of the DNA containing the promoter region, and recovering human growth hormone from the culture.

6. A recombinant DNA wherein a DNA coding for human growth hormone is linked to the 3'-terminal of a DNA containing a promoter region derived from *Bacillus brevis* and wherein a nucleotide sequence coding for an improved signal sequence R2L4 (SEQ ID NO: 6) is contained in a 3'-terminal site of the DNA containing the promoter region.

7. A *Bacillus brevis* carrying a recombinant DNA wherein a DNA coding for human growth hormone is linked to the 3'-terminal of a DNA containing a promoter region derived from *Bacillus brevis* and wherein a nucleotide sequence coding for an improved signal sequence R2L4 (SEQ ID NO: 6) is contained in a 3'-terminal site of the DNA containing the promoter region.

8. A process for the production of human growth hormone characterized by culturing *Bacillus brevis* according to claim 7, and recovering human growth hormone from the culture.

9. A process for the production of human growth hormone characterized by culturing *Bacillus brevis* 31-OK (FERM BP-4573) carrying a recombinant DNA wherein a DNA coding for human growth hormone is linked to the 3'-terminal of a DNA containing a promoter region derived from *Bacillus brevis* and wherein a nucleotide sequence coding for an improved signal sequence R2L4 (SEQ ID NO: 6) is contained in the 3'-terminal site of the DNA containing the promoter region, and recovering human growth hormone from the culture.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 73 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Bacillus brevis
    ( B ) STRAIN: 47 (FERM P-7224)

( i x ) FEATURE:
    ( A ) NAME/KEY: CDS
    ( B ) LOCATION: 1..69
    ( D ) OTHER INFORMATION: /note= "Signal Sequence of MWP of
        Bacillus brevis 47"

( x i ) SEQUENCE DESCRIPTION: SEQ ID NO:1:

```
ATG  AAA  AAG  GTC  GTT  AAC  AGT  GTA  TTG  GCT  AGT  GCA  CTC  GCA  CTT  ACT         48
Met  Lys  Lys  Val  Val  Asn  Ser  Val  Leu  Ala  Ser  Ala  Leu  Ala  Leu  Thr
 1              5                        10                       15

GTT  GCT  CCC  ATG  GCT  TTC  GCT  GCAG                                                 73
Val  Ala  Pro  Met  Ala  Phe  Ala
              20
```

( 2 ) INFORMATION FOR SEQ ID NO:2:

( i ) SEQUENCE CHARACTERISTICS:
    ( A ) LENGTH: 88 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc = "Synthetic DNA"

( v i ) ORIGINAL SOURCE:
    ( B ) STRAIN: Plasmid pNUR2L4

( i x ) FEATURE:
    ( A ) NAME/KEY: CDS
    ( B ) LOCATION: 1..84
    ( D ) OTHER INFORMATION: /note= "Improved Signal Sequence
        Derived from Signal Sequence of MWV of Baillus brevis 47"

( x i ) SEQUENCE DESCRIPTION: SEQ ID NO:2:

```
ATG  AAA  AAA  AGA  AGG  GTC  GTT  AAC  AGT  GTA  TTG  CTT  CTG  CTA  GCT  AGT         48
Met  Lys  Lys  Arg  Arg  Val  Val  Asn  Ser  Val  Leu  Leu  Leu  Leu  Ala  Ser
     25                       30                       35

GCA  CTC  GCA  CTT  ACT  GTT  GCT  CCC  ATG  GCT  TTC  GCT  GCAG                        88
Ala  Leu  Ala  Leu  Thr  Val  Ala  Pro  Met  Ala  Phe  Ala
 40                  45                       50
```

( 2 ) INFORMATION FOR SEQ ID NO:3:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( x i ) SEQUENCE DESCRIPTION: SEQ ID NO:3:

```
CACTGTTAAC  GACCCTTCTT  TTTTTCATGA  CCTTGTGTTC                                           40
```

( 2 ) INFORMATION FOR SEQ ID NO:4:

( i ) SEQUENCE CHARACTERISTICS:

```
         (A) LENGTH: 37 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Synthetic DNA"

(xi) SEQUENCE DESCRIPTION: SEQ ID NO:4:

CCGTGCACTA GCTAGCAGAA GCAATACACT GTTAACG                                        37

(2) INFORMATION FOR SEQ ID NO:5:

(i) SEQUENCE CHARACTERISTICS:
         (A) LENGTH: 23 amino acids
         (B) TYPE: amino acid
         (D) TOPOLOGY: linear (ii) MOLECULE TYPE: protein (xi) SEQUENCE DESCRIPTION: SEQ ID NO:5:

Met  Lys  Lys  Val  Val  Asn  Ser  Val  Leu  Ala  Ser  Ala  Leu  Ala  Leu  Thr
 1                  5                        10                       15

Val  Ala  Pro  Met  Ala  Phe  Ala
                20

(2) INFORMATION FOR SEQ ID NO:6:

(i) SEQUENCE CHARACTERISTICS:
         (A) LENGTH: 28 amino acids
         (B) TYPE: amino acid
         (D) TOPOLOGY: linear (ii) MOLECULE TYPE: protein (xi) SEQUENCE DESCRIPTION: SEQ ID NO:6:

Met  Lys  Lys  Arg  Arg  Val  Val  Asn  Ser  Val  Leu  Leu  Leu  Leu  Ala  Ser
 1                  5                        10                       15

Ala  Leu  Ala  Leu  Thr  Val  Ala  Pro  Met  Ala  Phe  Ala
                20                       25
```